US012582750B2

(12) United States Patent
　　　Ram-Liebig

(10) Patent No.:　US 12,582,750 B2
(45) Date of Patent:　Mar. 24, 2026

(54) METHOD FOR PRODUCING TRANSPLANTABLE ORAL MUCOSA TISSUE

(71) Applicant: MUKOCELL GMBH, Dortmund (DE)

(72) Inventor: Gouya Ram-Liebig, Neuss (DE)

(73) Assignee: MUKOCELL GMBH, Dortmund (DE)

( * ) Notice: Subject to any disclaimer, the term of this patent is extended or adjusted under 35 U.S.C. 154(b) by 528 days.

(21) Appl. No.: 18/249,167

(22) PCT Filed: Oct. 18, 2021

(86) PCT No.: PCT/EP2021/078762
　　　§ 371 (c)(1),
　　　(2) Date: Apr. 14, 2023

(87) PCT Pub. No.: WO2022/079312
　　　PCT Pub. Date: Apr. 21, 2022

(65) Prior Publication Data
　　　US 2023/0414834 A1　　Dec. 28, 2023

(30) Foreign Application Priority Data

Oct. 16, 2020　(EP) ..................................... 20202183

(51) Int. Cl.
　　　*A61L 27/36*　　　(2006.01)
　　　*C12N 5/071*　　　(2010.01)
(52) U.S. Cl.
　　　CPC ....... *A61L 27/3666* (2013.01); *A61L 27/3604* (2013.01); *A61L 27/3695* (2013.01); *C12N 5/0697* (2013.01); *C12N 2501/165* (2013.01); *C12N 2513/00* (2013.01); *C12N 2533/90* (2013.01)

(58) Field of Classification Search
　　　CPC .. A61L 27/36; A61L 27/3666; A61L 27/3604; A61L 27/3695; C12N 5/0697; A61F 2/0063; A61F 2/105
　　　See application file for complete search history.

(56) References Cited

U.S. PATENT DOCUMENTS

| 6,410,319 | B1 * | 6/2002 | Raubitschek | ........ | C12N 5/0636 435/372 |
| 2004/0033498 | A1 * | 2/2004 | Behrens | ............... | C12Q 1/6883 435/6.12 |

(Continued)

OTHER PUBLICATIONS

Castro et al., "Screening Circulating Tumor Cells as a Noninvasive Cancer Test in 3388 Individuals from High-Risk Groups (ICEL-LATE2)," Dis Markers, 2018:4653109 (May 28, 2018).

(Continued)

*Primary Examiner* — Vi X Nguyen
(74) *Attorney, Agent, or Firm* — McBee, Moore & Vanik IP, LLC

(57) ABSTRACT

The present invention relates to a method for producing transplantable oral mucosa tissue by selecting and choosing from oral mucosa biopsy, and to the use thereof as pharmaceutical composition, medicament or transplant or graft material, in particular for urethral reconstruction or cornea implantation. In particular, the invention relates to markers for identifying suitable transplantable oral mucosa tissue for the production of transplantable oral mucosa tissue, in particular for producing an autologous oral mucosa graft or tissue.

16 Claims, 5 Drawing Sheets

(56)                    References Cited

U.S. PATENT DOCUMENTS

2005/0164388 A1      7/2005  Son et al.
2007/0031890 A1*     2/2007  Wohlgemuth  .....  G01N 33/6863
                                                            435/7.1

OTHER PUBLICATIONS

Donnenberg et al., "Flow cytometric determination of stem/ progenitor content in epithelial tissues: An example from nonsmall lung cancer and normal lung," NIH Public Access Author Manuscript, vol. 83A, No. 1, pp. 141-149 (Jan. 1, 2013).

Elahi et al., "Noninvasive Optical Assessment of Implanted Engineered Tissues Correlates with Cytokine Secretion," Tissue Engineering. Part C, Methods Dec. 2008, vol. 24, No. 4, pp. 214-221 (Apr. 1, 2018).

Holmes et al., The vascular endothelial growth factor (VEGF) family: angiogenic factors in health and disease, Genome Biol 6, 209 (2005).

Kisselbach et al., "CD90 Expression on human primary cells and elimination of contaminating fibroblasts from cell cultures," Cytotechnology, vol. 59, No. 1, pp. 31-44 (Mar. 19, 2009).

Mcguire et al., "Living cell-based regenerative medicine technologies for periodontal soft tissue augmentation," Journal of Periodontology, vol. 91, No. 2, pp. 155-164 (Sep. 24, 2019).

Moharamzadeh et al., "Tissue-engineered Oral Mucosa: a Review of the Scientific Literature," Journal of Dental Research, vol. 86, No. 2, pp. 115-124 (Feb. 1, 2007).

Senger et al., "VEGF expression by epithelial and stromal cell compartments: resolving a controversy," Am J Pathol., 157(1):1-3 (Jul. 2000).

International Search Report issued in International Application No. PCT/EP2021/078762 (5 pages) (Jan. 26, 2022).

* cited by examiner

A

B

Line 1: 1-3, line 2: 4-6, line 3: 7-9

METHOD FOR PRODUCING TRANSPLANTABLE ORAL MUCOSA TISSUE

CROSS-REFERENCE TO RELATED APPLICATIONS

This application is a National Stage entry of International Application No. PCT/EP2021/078762, filed 18 Oct. 2021, which claims priority to European Patent Application No. 20202183.8, filed 16 Oct. 2020.

BACKGROUND

Field

The present invention relates to a method for producing transplantable oral mucosa tissue by selecting and choosing from oral mucosa biopsy, and to the use thereof as pharmaceutical composition, medicament or transplant or graft material, in particular for urethral reconstruction or cornea implantation. In particular, the invention relates to markers for identifying suitable transplantable oral mucosa tissue for the production of transplantable oral mucosa tissue.

In general, the subject invention relates to disciplines of tissue engineering, tissue regeneration and regenerative medicine combining bioengineering methods with the principles of life sciences to understand the structural and functional relationships in normal and pathological mammalian tissues. The overall goal of these disciplines is the development and ultimate application of biological substitutes to restore, maintain, or improve tissue functions. Thus, it is possible to design and manufacture a bioengineered tissue in a laboratory.

Description of Related Art

Bioengineered tissues can include cells that are usually associated with a native mammalian or human tissues and synthetic or natural matrix scaffolds. The new bioengineered tissue must be functional when grafted or transplanted onto a host and be permanently incorporated within the host's body or progressively bio-remodelled by cells from the bioengineered tissue or recipient host.

"Transplantable oral mucosa tissue" means the production ex-vivo or with the aid of an in-vitro technique, wherein the produced tissue corresponds largely to the native tissue or is identical to the native tissue. In the sense of the invention the transplantable oral mucosa tissue corresponds largely to the native tissue for example in relation to the expression or expression pattern of the extracellular matrix, for example in relation to the expression or expression pattern of structural proteins or proteids.

The expression or expression pattern can be detected for example histologically or immunohistologically.

SUMMARY

The transplantable oral mucosa tissue produced by the method according to the invention is similar to the native tissue in respect of the phenotype, composition and protein expression.

Thus, the present invention refers to methods for producing an autologous oral mucosa graft or tissue comprising;
a.) removing or obtaining a biological sample from the oral cavity of a subject or patient, wherein the biological sample comprises original oral mucosa cells and b.) culturing the original oral mucosa cells from the tissue sample to generate cultured oral mucosa cells. After achieving confluency, the cells are detached and again cultured on the surface of a support.

DETAILED DESCRIPTION OF A PREFERRED EMBODIMENT

Figure 1:
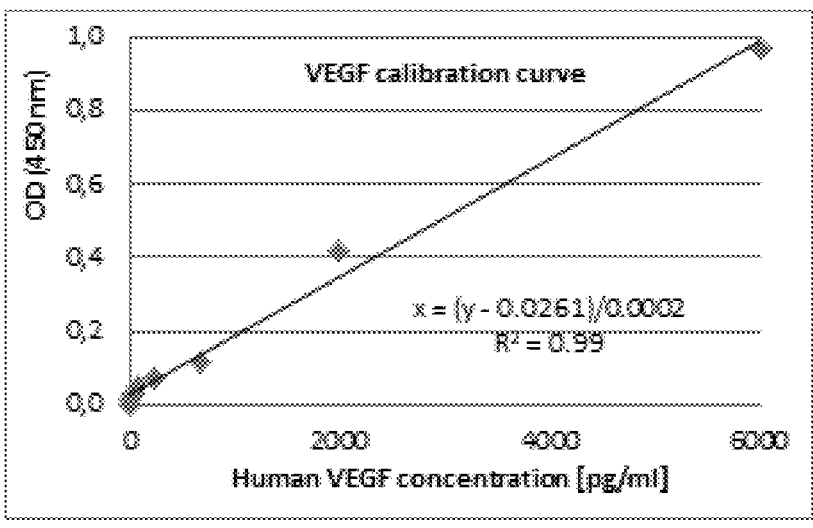
FIGS. 1-7 depict embodiments as described herein.
Figure 1:
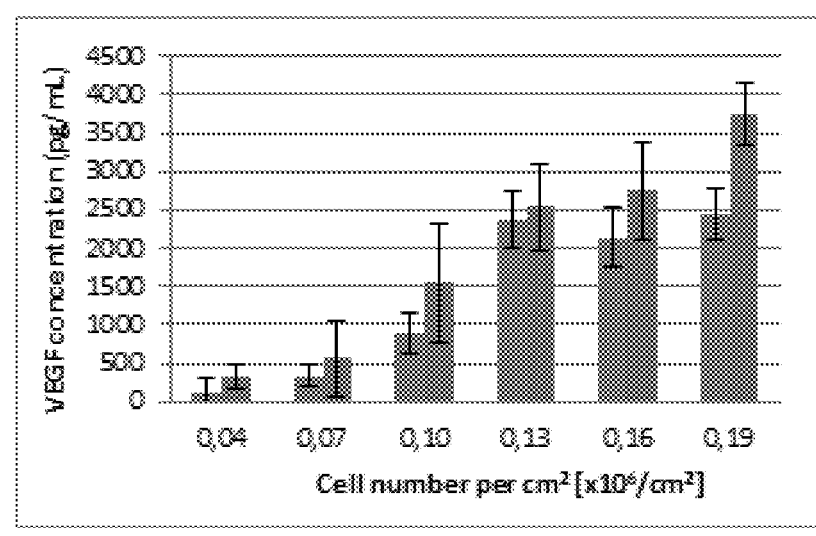

In a preferred embodiment the removed biological sample is an area of about 40 mm×80 mm of oral mucosa tissue from a subject or patient.

There is thus a great need to provide oral mucosa tissue which have a sufficient quality and can produce a suitable transplantable oral mucosa tissue which corresponds to the native tissue, such that success of the treatment can be expected. This treatment success is largely dependent on the quality of the transplantable oral mucosa tissue.

The object of the invention is therefore to provide an improved transplantable oral mucosa tissue, in particular having improved properties, in particular sufficient quality, such as identity with native oral mucosa tissue and having improved quality such that high-quality transplants can be obtained, in particular for the successful treatment and therapy, in particular of oral mucosa defects and urethral stricture, in particular anterior urethroplasty, corneal diseases, in particular cornea implantation.

The inventors were surprisingly able to identify markers for the isolated oral mucosa tissue which allow a sufficient quality for the production of transplantable oral mucosa tissue.

The markers according to the invention allow in particular the determination of oral mucosa cell potency ("potency markers") of the isolated oral mucosa tissue in a culture to the native oral mucosa tissue.

A suitable oral mucosa cell potency in turn allows the production of suitable transplantable oral mucosa tissue, since an improved treatment is achieved.

In a further embodiment the markers according to the invention allow the determination of the purity or impurity of the isolated oral mucosa tissue ("purity or impurity markers").

The aforementioned markers ensure a sufficient quality and therefore constitute "quality markers".

The invention therefore relates to a method for the selection of oral mucosa tissue for the production of transplantable oral mucosa tissue, wherein at least one quality marker(s) is/are determined.

The method according to the invention for the selection of oral mucosa tissue for the production of transplantable oral mucosa tissue comprises, in a first step, that the oral mucosa cells derived from a tissue biopsy are multiplied in a culture, preferably cultured in sterile culture flasks, and, in a second step the cells are cultured on the surface of a support.

Hence, the invention refers to a method for selecting oral mucosa tissue for the production of transplantable oral mucosa tissue, wherein the cells are cultured on the surface of a support, characterised in that at least one
   potency marker is selected from at least one vascular endothelial growth factor (VEGF) having a threshold value of more than or equal to 10 pg/ml in the supernatant after 24 h of seeding on the surface
   and at least one
   purity marker is selected from at least one acidic and basic (Type I and II) subfamilies of cytokeratins, wherein the amount of epithelial cells is more than or equal to 70%, preferably 80%, most preferably more than or equal to 95%, and/or at least one impurity marker is selected from at least one CD90, wherein the amount of non-epithelial cells is less than or equal to 30%, preferably less than or equal to 20%, most preferably less than or equal to 5%, wherein the markers are determined in vitro.

According to the invention such a "support" (synonymous: carrier) shall mean preferably a membrane, preferably a dissolvable, self-dissolvable membrane or biodegradable membrane or a glass, in particular a cover slip, wherein the oral mucosa tissue is fixed.

In a preferred embodiment of the invention the dissolvable, self-dissolvable membrane consists of one or more biodegradable polymers, preferably biocompatible polymers or water-soluble polymers, in particular of biological or non-biological origin, preferably polymers such as alpha-hydroxy acids, lactic acid and/or glycolic acid, polylactides, polyglycolides, polylactide-co-glycolides, and copolymers with polyethylene glycol, polyanhydrides, poly(ortho)esters, polyurethanes, Polyglycolic acids, Polylactic acids, Poly-caprolactone, polybutyric acids, polyvaleric acids, polylac-tide-co-caprolactones, polyvinyl pyrrolidone (PVP), gly-cans, glycosaminoglycans and polysaccharides, such as pullulan, hyaluronan, gellan, alginate, cellulose.

In a further preferred embodiment of the invention the biodegradable or biocompatible membrane is selected from the group of chitosan, alginate, and collagen and any derivative thereof.

If required, the said structures are completed with additives, plasticizers, emulsifiers, and crosslinking agents.

If required, the support may be changed, and the oral mucosa tissue is refixed.

Said "vascular endothelial growth factor (VEGF)" is known to play a key role in tissue regeneration and wound healing by the stimulation of microvascular growth and blood perfusion. It belongs to a sub-family of platelet-derived growth factors known to be involved in vasculo-genesis and angiogenesis by increasing microvascular endothelial cell migration, branching and capillary sprouting (Holmes, D.; Zachary, I. "The vascular endothelial growth factor (VEGF) family: angiogenic factors in health and disease" Genome Biol., 2005, 6(2):209).

Said "CD90 (also called Thy-1 antigen)" is a conserved cell surface glycoprotein having a glycosylphosphati-dylinositol (GPI) anchor consisting of a single IgSF variable domain and specific for non-epithelial cells like fibroblasts. Epithelial cells are negative for CD90. Hence, CD90 is an appropriate impurity marker in accordance with the invention. CD90 is detectable or recognized by antibodies (mono-clonal or polyclonal), which are commercially available (e.g. antibodies.com u.a.). Kisselbach et al. (Kisselbach, L; Merges, M; Bossie, A; Boyd, A. CD90 Expression on human primary cells and elimination of contaminating fibroblasts from cell cultures. Cytotechnology. 2009 January; 59(1): 31-44) describe that CD90 can be efficiently used as a specific maker for fibroblasts to detect fibroblastic contami-nations and therefore verify cell culture purity. Hereto, CD90 immunofluorescence labelling can be used to detect protein expression in a panel of various human primary cell lines. CD90 expression can be subsequently detected by flow cytometry.

Said "acidic and basic (Type I and II) subfamilies of cytokeratins" are present in human epithelia and detectable or being recognized by so called pan-cytokeratin antibodies (Castro, J; Sanchez, L; Nunez, MT; Lu, M; Castro, T; Sharifi, HR; Ericsson, C. Screening Circulating Tumor Cells as a Noninvasive Cancer Test in 3388 Individuals From High-Risk Groups (ICELLATE2). Dis Markers. 2018 May 28; 2018:4653109; Donnenberg, VS; Landreneau, RJ; Pfe-ifer, ME; Donnenberg, AD. Flow Cytometric Determination of Stem/Progenitor Content in Epithelial Tissues: An Example From Nonsmall Lung Cancer and Normal Lung. Cytometry A. 2013 January; 83(1):141-9), which are com-mercially available (e.g. antibodies.com u.a.).

Pan-cytokeratin belongs to a family of intermediate fila-ment proteins present in human epithelial tissue. To date there are at least 20 different individual human cytokeratins known, ranging between 40-68 kDa regarding their molecu-lar weight.

For example, in a preferred embodiment, the so called "Pan Cytokeratin Monoclonal Antibody (AE1/AE3), Alexa Fluor 488, eBioscience™" recognizes a wide area of the cytokeratin family: AE3 detects the 65 to 67 triplet, 64, 59, 58, 56, 54 and 52 kD proteins also known as cytokeratin 1-8 as well as the 56.5, 54', 50, 50', 48, and 40 kDa proteins known as cytokeratin 10, 14-16 and 19 which are detected by AE1.

According to the invention, the VEGF concentration is continuously increased into the culture medium (superna-tant) in a time dependent manner after seeding. Furthermore, said VEGF secretion correlates with the density of the cells seeded onto the membrane and being consistently released by the cells within 24 h or 48 h post-seeding or after incubation.

It should be noted, that VGEF expression may vary from the presence of appropriate cells and cell density. As found by Senger et al. (VEGF expression by epithelial and stromal cell components, American Journal of Pathology, Vol. 157, No. 1, July 2000) VEGF-mRNA is expressed by epithelial cells of keratinocytes in skin wound healing, which are known as a principal source of releasing VEGF. In contrast hereto, stromal cells such as dermal fibroblasts express no or comparatively minimal levels of VEGF-mRNA.

Particularly, the inventors have found that after seeding the support should have at least a cell density of $1.0 \times 10E6$ to $1.6 \times 10E6$ cells, preferably at least $1.3 \times 10E6$ on an area of 2.8 cm×3.8 cm, i.e. app. 10 cm$^2$ or at least a density of at least $1.0 \times 10E5$ to $1.6 \times 10E5$ cells, preferably at least $1.3 \times 10E5$ cells/cm$^2$.

Such a chosen and selected cell-density guarantees advan-tageously the continuous secretion/release of VEGF into the culture medium and supporting the required threshold value of more than or equal to 10 pg/ml in the supernatant in accordance with the invention.

Hence, after clinical implantation of the devices in 10 patients and a successful follow-up of 48 months, the inventors found out, that surprisingly, a threshold value of more than or equal to 10 pg/ml of VEGF in the supernatant after 24 h of seeding on the surface allows to specify a sufficient potency of the isolated oral mucosa tissue and related cells. As outlined in the examples such cells are capable to produce endothelial cell tubes in the oral mucosa tissue.

The in vitro determination of the markers according to the invention is preferably achieved by determining the activity of these markers and also the level of the activity in the isolated oral mucosa tissue, which for example can be determined routinely by ELISA, staining tests; see the examples.

In accordance with the invention the markers show activity in the method according to the invention, thus demonstrating their suitability as markers as indicated in the examples.

Within the scope of this invention the term "selection" means that, for example, oral mucosa tissue that have no activity of the markers according to the invention or that have a relatively low activity or activity level compared to other oral mucosa tissue are discarded. A person skilled in the art is capable of distinguishing between a stronger activity and a weaker activity for one or more oral mucosa tissue based on the obtained activity patterns, and of choosing such oral mucosa tissue accordingly.

The invention therefore relates to a method for selecting oral mucosa tissue for the production of transplantable oral mucosa tissue, wherein the markers according to the invention are determined.

In a further preferred embodiment, during the course of the performed determinations of the purity marker, the proportion of fibroblasts as impurity in the isolated oral mucosa after multiplication in relation to the total number of cells or amount is less than or equal to 20%, preferably less than or equal to 5% and the purity in the isolated oral mucosa after multiplication in relation to the total number of cells or amount of epithelial cells is more than or equal to 70%, preferably 80%, most preferably 95%.

In a further preferred embodiment, during the course of the performed determinations of the purity marker, the proportion of lymphocytes and adipocytes as impurity in the isolated oral mucosa after multiplication in relation to the total number of cells or amount is less than or equal 2%, preferably less than or equal 1% or 0%.

The method according to the invention allows the selection of oral mucosa tissue that are chosen specifically for an oral mucosa tissue to be transplanted. This is based on the particular properties of the markers according to the invention, specifically quality marker, encompassing potency marker or purity marker. Consequently, oral mucosa which have a specific quality are chosen, and corresponding gene products or proteins can be easily detected for example by means of PCR, antibodies, histological or immunohistological examination, etc.

The invention therefore relates to isolated oral mucosa tissue, obtainable by a method according to the invention.

Hence, the present invention refers to isolated oral mucosa tissue, wherein the proportion of fibroblasts in the isolated oral mucosa tissue in relation to the total cell number is less than or equal to 5%, or less than or equal to 1% and/or, wherein the proportion of lymphocytes and adipocytes as impurity in the isolated oral mucosa after multiplication in relation to the total number of cells or amount is less than or equal 2%, preferably less than or equal 1% or 0%.

Also comprised is a transplantable oral mucosa tissue, preferably in the form of a graft or transplant, in particular in the form of a drug or medicinal product (so called ATMP) or in the form of a pharmaceutical composition containing such oral mucosa, in particular for use in the treatment of oral mucosa defects and diseases selected from vascular disorders, including diabetic foot, ulcer due to atherosclerosis, as well as diseases which require additional tissue for reconstruction such as, and not limited to skin burns, shrunken bladder, bladder dystrophy, small bladder after excision of bladder tumors, esophageal atresia, missing tissue after excision of esophagus tumor, ureteral stricture, ureteral tumor, urethra diseases, in particular urethral stricture, urethra malformation, hypospadias, corneal diseases, in particular limbal stem cell deficiency, cornea injury. A graft or transplant may have a scaffold or matrix.

However, in a preferred embodiment the isolated or obtained oral mucosa tissue, in particular for use as outlined above, is fixed on the support or refixed on the support, wherein the support is a dissolvable, self-dissolvable membrane or a biodegradable membrane as outlined above. Hereto, it is advantageously that after application, in particular grafting the said membrane is removable, in particular by dissolution.

As used herein, a "graft (transplant)" refers to a cell, cells, tissue or organ that is implanted into an individual, typically to replace, correct or otherwise overcome a defect. A graft may further comprise a scaffold or matrix. The tissue or organ may consist of cells that originate from the same individual, subject, in particular a patient; this graft is referred to herein by the following interchangeable terms: "autograft", "autologous transplant", "autologous implant" and "autologous graft". A graft comprising cells from a genetically different individual of the same species is referred to herein by the following interchangeable terms: "allograft", "allogeneic transplant", "allogeneic implant" and "allogeneic graft". In a preferred embodiment the graft (transplant) shall be obtained and provided from the same subject or patient.

As used herein, "scaffold" and "matrix" are used interchangeably and refer to a structure, comprising a biocompatible material that provides a surface suitable for adherence and proliferation of cells. A scaffold may further provide mechanical stability and support. A scaffold may be in a particular shape or form to influence or delimit a three-dimensional shape or form assumed by a population of expanded cells. Such shapes or forms include, but are not limited to, films (e.g. a form with two-dimensions substantially greater than the third dimension), ribbons, cords, sheets, flat discs, cylinders, spheres, 3-dimensional amorphous shapes, etc.

In a further preferred embodiment of the invention the transplantable oral mucosa tissue according to the invention is administered to a patient with the aid of an applicator.

Hence, the present invention refers to an applicator comprising transplantable oral mucosa tissue like a graft or transplant obtainable according to the disclosed method.

The transplanted oral mucosa tissue may preferably be kept in the form of a pharmaceutical composition in a physiological saline solution together with further auxiliaries and additives.

Unless defined otherwise, all technical and scientific terms used herein generally have the same meaning as commonly understood by one of ordinary skill in the art to which this invention belongs. Generally, the nomenclature used herein and the laboratory procedures in cell culture, analytics are those well-known and commonly employed in the art.

The following drawings and examples serve to explain the invention, but without limiting the drawings and examples.

EXAMPLE 1

In order to qualify VEGF as a parameter for potency testing according to the invention, the inventors have performed a dosing study using different cell seeding densities and using an ELISA method for VEGF quantification.

Cultured oral mucosa cells that were isolated from an oral mucosa biopsy of an adult human donor were used for this study. Biopsy taking and processing as well as cell culturing were performed according to standard protocols. The cells of the final cell suspension were characterized by immunocytochemical staining using antibodies against cytokeratin as a marker for epithelial cells and against CD90 as a marker for other cell types like fibroblasts to exclude substantial contamination by non-epithelial cells. Several biodegradable matrices were seeded with increasing cell numbers of the finally harvested cell suspension. For each applied cell density membranes were prepared in triplicates. Each three membranes were seeded with six different cell densities from $0.04 \times 10E6 \pm 25\%$ cells/cm$^2$ to $0.19 \times 10E6 \pm 25\%$ cells/cm$^2$.

The used ELISA kit for quantitative VEGF determination was intended for samples with human VEGF concentrations up to 6,000 pg/ml. A linear correlation up to this concentration was found using the standards provided with the test kit. The corresponding calibration curve together with its equation is provided in FIG. 1. The FIG. 1 also shows the result of VEGF determination in the samples taken after 24 h and 48 h from the supernatant of the cell seeded membranes. The concentrations of VEGF found after 48 h incubation were higher than those found after 24 h incubation. Paired t-test analysis revealed a highly significant difference between the VEGF concentrations found after 24 h and 48 h incubation ($p < 0.0001$).

The following results were found regarding the effect of cell seeding density and the dependent release of VEGF: After 24 h incubation statistically significant differences of VEGF concentrations were found in medium samples from membranes seeded with 0.04 vs. $0.07 \times 10E6 \pm 25\%$ cells/cm$^2$, 0.07 vs. $0.10 \times 10E6$ cells/cm$^2 \pm 25\%$ and 0.10 vs. $0.13 \times 10E6 \pm 25\%$ cells/cm$^2$. No significant difference was found for the VEGF concentrations in medium samples taken from degradable matrices seeded with 0.13 vs. $0.16 \times 10E6 \pm 25\%$ cells/cm$^2$ or 0.16 vs. $0.19 \times 10E6 \pm 25\%$ cells/cm$^2$, respectively.

Analysis of the medium samples taken 48 h after incubation showed a slightly different result. No significant difference was found for the difference in VEGF concentration between medium samples taken from degradable matrices seeded with 0.04 vs. $0.07 \times 10E6 \pm 25\%$ cells/cm$^2$. Significant differences regarding VEGF concentration were found between medium samples taken from membranes seeded with 0.07 vs. $0.10 \times 10E6 \pm 25\%$ cells/cm$^2$, as well as 0.10 vs. $0.13 \times 10E6 \pm 25\%$ cells/cm$^2$. The difference between the VEGF concentration in medium samples taken from matrices seeded with 0.13 vs. $0.16 \times 10E6 \pm 25\%$ cells/cm$^2$ was not significant.

However, the difference in VEGF concentration between medium samples taken from matrices seeded with 0.16 vs. $0.19 \times 10E6 \pm 25\%$ cells/cm$^2$ was significant.

Overall, a density-dependent increase of VEGF concentrations was found for cell seeding densities up to $0.10 \times 10E6 \pm 25\%$ cells/cm$^2$ but not or to a lower extent for higher cell seeding densities. Maximum VEGF concentrations were already reached at a cell seeding density of $0.13 \times 10E6 \pm 25\%$ cells per cm$^2$ in accordance with the present invention.

EXAMPLE 2

ELISA: To determine the concentration of VEGF as a parameter for potency testing 1 ml of the supernatant culture media from cultured cells on biodegradable matrices are taken off and determined per ELISA.

The VEGF measurement is based on a commercial ELISA kit (R&D Quantikine Elisa for human VEGF, catalog #DVE00/SVE00/PDVE00).

To conduct the assay, aliquots of the samples to be tested and of the VEGF standards are added in triplicate to the wells of the anti-human VEGF coated microwell plate. The plate is then incubated 2.5 h at room temperature. After washing four times with washing buffer, the prepared biotinylated detection antibody is added to the wells. The antibody is incubated one hour at room temperature followed by four times washing and the addition of the prepared streptavidin solution. After incubation for 45 minutes at room temperature, the plate is washed four times and the TMB substrate reagent is added to the wells. After 15 minutes incubation the reaction is stopped by adding the stop solution to the wells. The absorbance at 450 nm is measured by means of a microplate reader immediately after addition of the stop solution. Concentrations of VEGF are calculated using a calibration curve. As positive control, endothelial cell specified culture medium of PromoCell is used. As negative control, the same medium without supplements is used.

Angiogenesis-Tube Formation Assay:

It is known that angiogenesis is characterized by several cellular events including endothelial cell migration, invasion and differentiation into capillaries. In vitro endothelial tube formation assays are used as a model for studying endothelial differentiation and modulation of endothelial tube formation by antiangiogenic agents. Image acquisition and quantification of fluorescently labelled cells are achieved using appropriate software. In our case, human endothelial stem cells are seeded on 6-well plate and attached for 48 h in growth medium and differentiation of the cells using differentiation medium. Afterwards, endothelial cells are seeded onto Corning® Matrigel® Matrix where they are feeded with conditioned medium taken from oral mucosa cell cultures on biodegradable membranes. Due to the presence of VEGF in the conditioned medium, endothelial cells are induced to form angiogenic tubes in the 3D Matrigel. Angiogenic potency is determined by software assisted quantitative assessment of microvessel formation (Carpentier, G. Angiogenesis Analyzer for ImageJ. ImageJ News 9 Nov. 2012).

For the investigation of potency of cultured oral mucosa cell on biodegradable matrices, The conditioned culture media from several batches were tested in both ELISA and angiogenic tube formation assays.

The results of the VEGF ELISA assay are shown in Table 4.

TABLE 4

VEGF concentrations in tested culture media. All samples show a value of more than 10 pg/ml, except No. 3 and 4, which were much lower. The two latter conditioned media (2 and 3) were thermally pretreated, resulting in the denaturation of VEGF.

| Sample No. | VEGF [pg/ml] | STDV [pg/ml] |
| --- | --- | --- |
| 1 | 644.9 | 4.9 |
| 2 | 194.4 | 1.8 |
| 3 | 1.9 | 0.2 |
| 4 | 2.7 | 0.2 |
| 5 | 432.0 | 5.7 |
| 6 | 559.5 | 2.3 |
| 7 | 528.9 | 2.5 |
| 8 | 425.8 | 5.7 |

Figure 3:
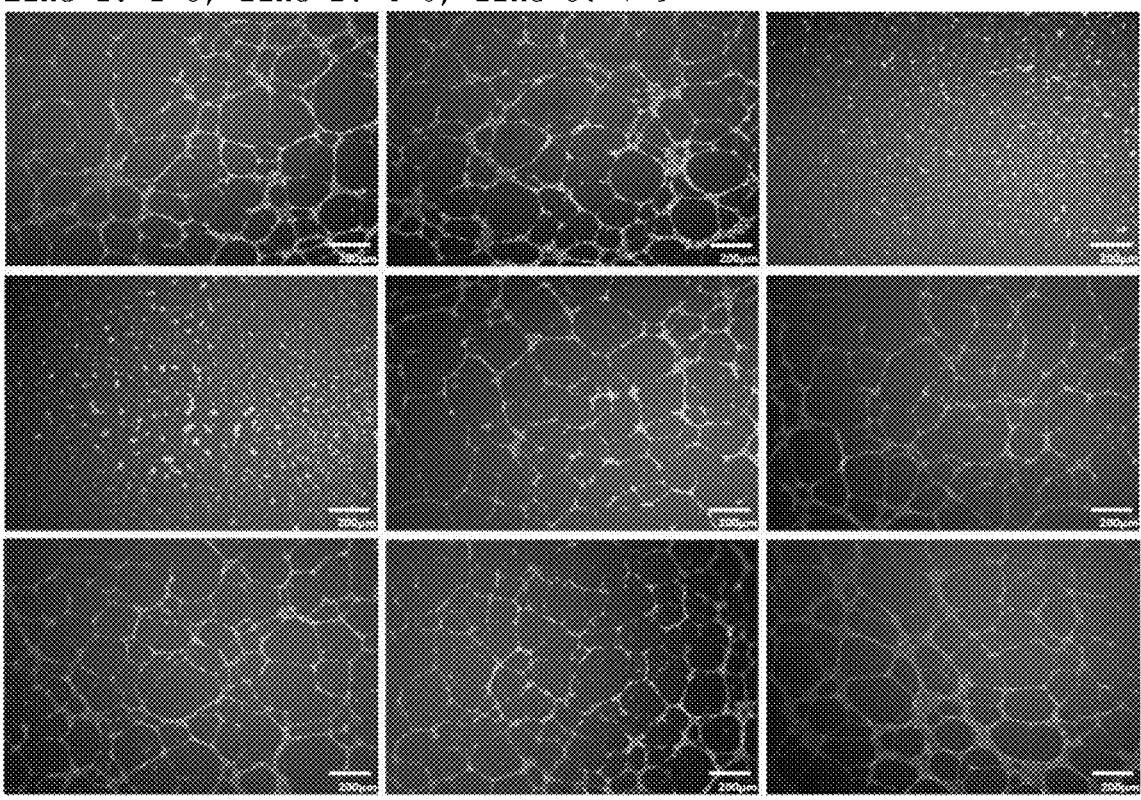
Figure 4:
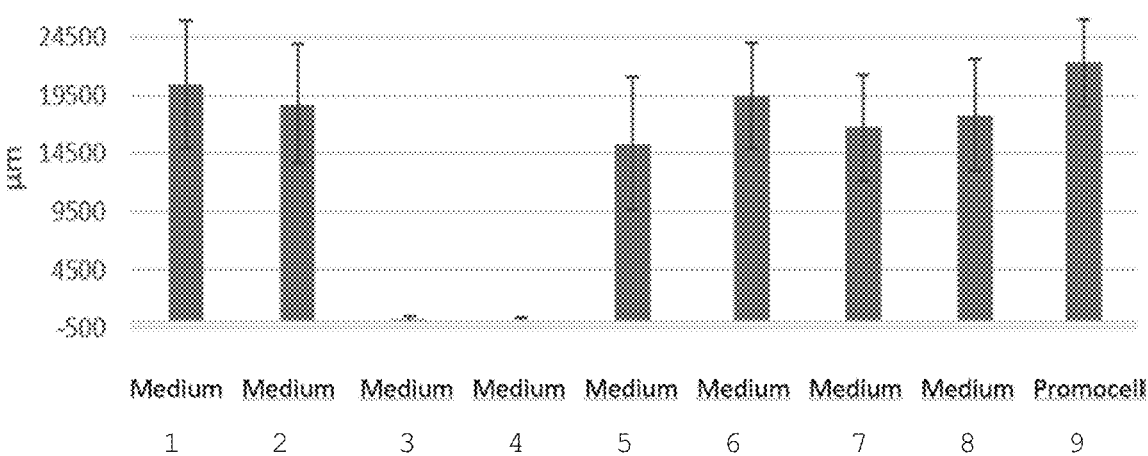

The same culture media were used in the tube formation assay. Results are shown in FIG. 3 and FIG. 4.

These results indicate that the culture media conditioned by the cells seeded on the biodegradable membranes exert an angiogenetic effect on the HUVEC cells, comparable to the highly specific and inducing angiogenetic endothelial medium from PromoCell which was used as a positive control. Generally, it has to be noted that despite the fact that glucose, insulin and other substances are already consumed by cultured oral mucosa cells in media after two days of incubation on the membrane, the effect is comparable to the positive control. Interestingly, two media samples (No. 3 and 4) did not meet the threshold value set regarding VEGF concentration (≥10 pg/ml) in accordance with the invention. The same two media showed no microscopic detectable tube formation (FIG. 3) and no branching (FIG. 4) as well. These two media were thermally treated prior the ELISA and angiogenic assay, resulting in the denaturation of VEGF.

The following table (Table 5) summarizes the data obtained for the stated samples for ELISA and Angiogenesis assay. The correlation efficient as well as the corresponding p-values were calculated based on these results and are also indicated in the table.

For detection on impurities, CD90 staining was used for all 100 patients for the detection of any existing fibroblasts.

For each analysis approx. 500.000 cells were fixed with 1 mL 0.01% formalin and post-fixed with ice-cold ethanol. The fixed cells were then permeabilized with 0.1% Triton/ 1% BSA in PBS, and aliquots of the permeabilized cells were stained with a 1:500 dilution of the AE1/AE3 or CD90 antibody (Dako, M3515) in 1% BSA or with the respective buffer control. The cells were differentiated with an Alexa Fluor 488-coupled goat-anti-mouse IgG and resuspended in 1% BSA for FACS analysis (one-colour histograms).

Figure 6:
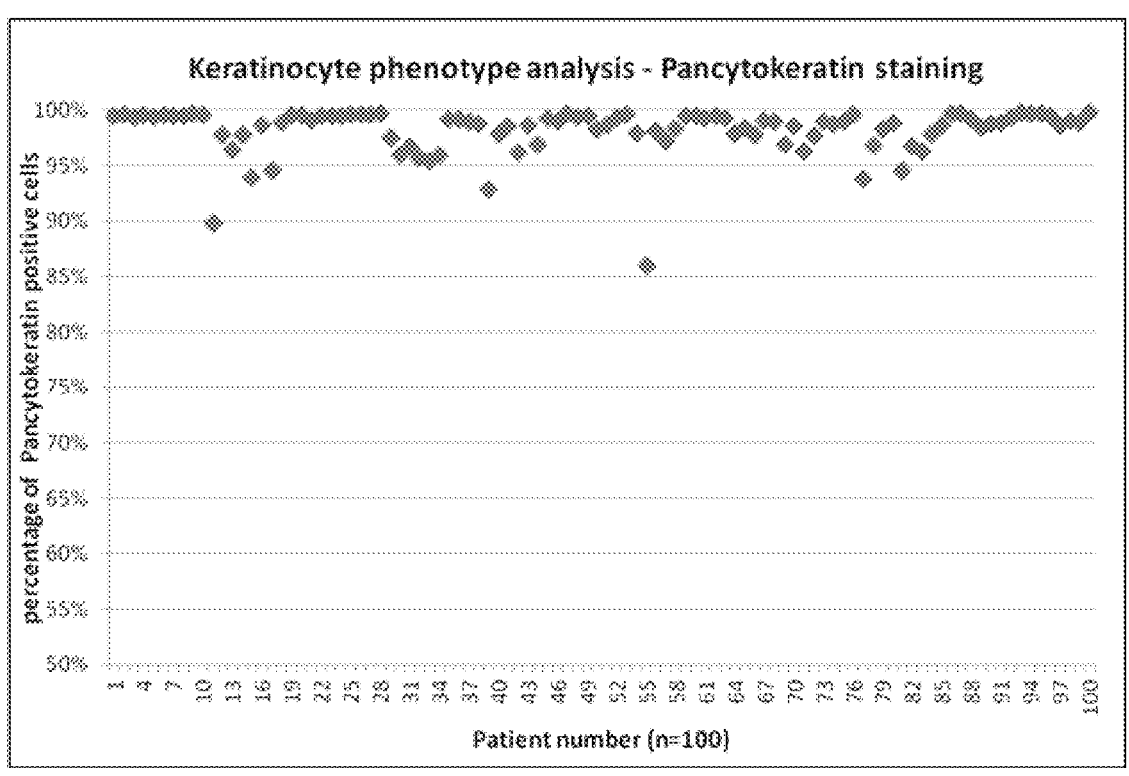

FACS analysis and evaluation of data was performed using a Becton Dickinson FACS Calibur® device and the CellQuest Pro® software package. FIG. 6 shows an example of FACS results for cytokeratin, obtained for the first analysed batch in this series of experiments.

Detection of fibroblastic impurities and confirmation of epithelial identity in oral mucosal cells via immunocytochemistry:

To confirm the results of FACS analysis, immunofluorescence staining was additionally carried out with a keratinocyte specific marker (Pan-Cytokeratin) for identity and CD90 antibody for quantifying potential cellular impurities in terms of fibroblasts

TABLE 5

Calculation of the correlation of VEGF ELISA and Angiogenesis assay.

| | ELISA | | Angiogenesis | |
| --- | --- | --- | --- | --- |
| Sample ID | VEGF [pg/ml] | Nr. of Segments | Nr. of meshes | Total branching length [μm] |
| 1 | 644.9 | 219.83 | 45.75 | 20434.71 |
| 2 | 194.4 | 174.08 | 30.42 | 18765.30 |
| 3 | 1.90 | 0.62 | 0.38 | 286.48 |
| 4 | 2.70 | 7.20 | 1.40 | 176.74 |
| 5 | 432 | 128.43 | 20.71 | 15350.65 |
| 6 | 559.5 | 169.50 | 30.44 | 19436.22 |
| 7 | 528.9 | 140.95 | 23.27 | 16758.92 |
| 8 | 425.8 | 151.00 | 23.00 | 17866.69 |
| Correlation | | 0.997 | 0.980 | 0.985 |
| p-value | | 0.001 () | 0.007 () | 0.005 (**) |

To assess a potential correlation of VEGF ELISA data with angiogenesis measurements, angiogenesis values (nr. of segments, nr. of meshes, and total branching length) were compared to the corresponding VEGF concentrations. Interestingly, all values showed a significant correlation between ELISA and angiogenesis measurements. These results indicate that VEGF ELISA can be used as a marker assay for the potency measurements of the oral mucosa cells according to the invention.

EXAMPLE 3

Phenotypic characterization of oral mucosal cells, Keratinocytes-via flow cytometry (FACS) Investigation of cell identity (epithelial cells≥70%) and purity (Fibroblasts≤30%)

The inventors conducted a phenotypic characterization of in vitro expanded oral mucosal cells (22±5 days of culture) encompassing 100 independent batches. The purpose of this study was the confirmation of identity of cultivated human oral mucosal cells using flow cytometry. Pan-cytokeratin antibody was used to identify epithelial cells (analysis of cell identity). Cytokeratins, a group comprising at least 29 different proteins, are characteristic of epithelial cells.

The used pan-cytokeratin antibody was a cocktail of two mouse monoclonal antibodies (AE1/AE3) (supra).

Applied method of cell staining with pan-cytokeratin and CD 90 for immunocytochemical analysis determination of purity and Identity of cells:

Wash the cells 3×1 min with PBS solution

Remove PBS.

Fix the cells by adding 4% PFA or acetone for 10 min at RT.

Remove 4% PFA or acetone solution

Wash the cells 3×1 min with PBS solution

Incubate the cells with 100 μl antibody (CD90 with concentration 1:50 and PCK with concentration 1:100 at the same time) solution in each well at RT for 4 hrs. in the dark Incubated the cells with 100 μl of Hoechst staining solution for 3 min at RT.

The results of immune-cytochemical analysis in immunofluorescence microscopy is in accordance with the results of FACS confirming the epithelial identity of cells and a fibroblastic impurity of less than 5% (cf. FIG. 6).

FIG. 1: Quantitative determination of VEGF concentrations. The figure A shows the results for samples with known VEGF concentration and the measured absorbance. The corresponding calibration curve and the equation are indicated in the picture. The figure B depicts the calculated means and standard deviations of measured VEGF concentrations of supernatant culture medium taken from membranes seeded with increasing cell densities (indicated on the x-axis). Culture medium was taken after either 24 h (left columns) or 48 h (right columns), respectively.

Figure 2:
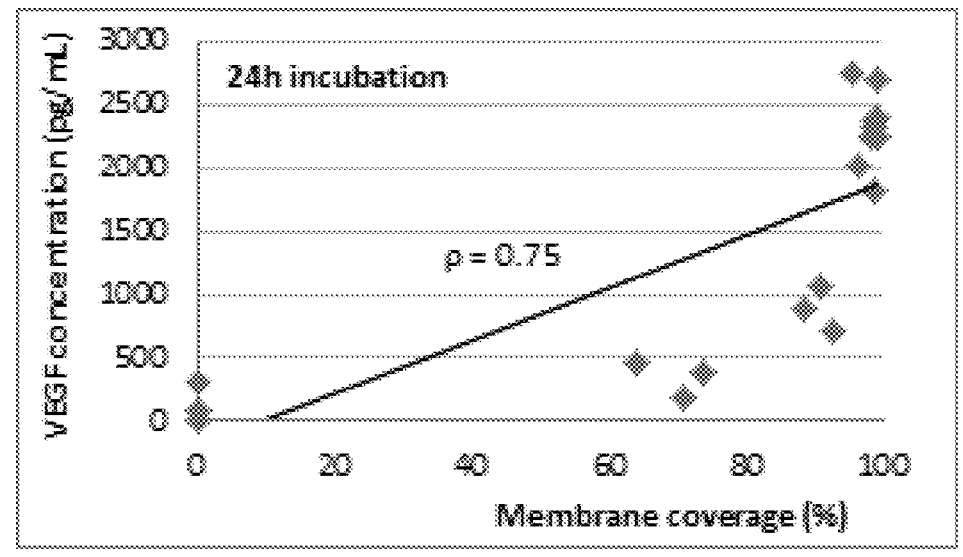
Figure 2:
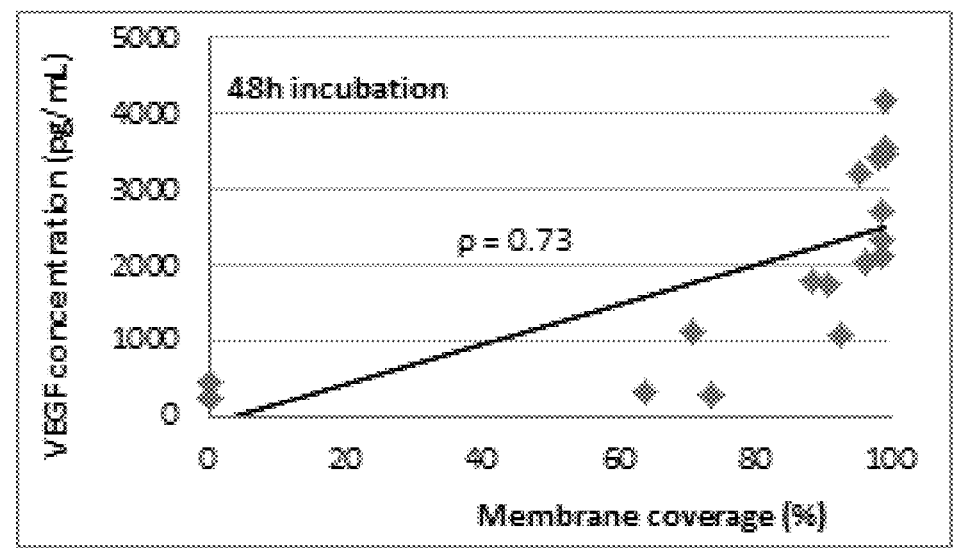

FIG. 2: Correlation between VEGF release and cell coverage of the membrane. The VEGF concentrations of the indicated samples were measured after either 24 h (figures on the left side) or 48 h (figures on the right side). A positive correlation was found in both cases. The corresponding correlation coefficient (p) for each calculated linear correlation is indicated.

FIG. 3: Tube formation assay with culture medium from 8 batches. Human Umbilical Vein Endothelial Cells (HU-VEC) were cultivated until proper number in Endothelial Cell Growth Medium (PromCell GmbH). HUVEC cells were detached from the cell culture flasks using Trypsin/EDTA into single cell suspension. Corning® Matrigel® was carefully thawed and coated in the bottom of 48-well plate. 150 µl cell suspension with $8 \times 10^4$ cells were seeded unto the Matrigel surface. After 8 hours, HUVEC formed angiogenic tubes, and were stained with Calcein AM (Live Cells, Green) and Propidium Iodide (Dead Cells, Red). Fluorescence Photos were taken in the channel of Green, Red and Bright Field. Batches from left to right, from top to bottom: 1, 2, 3, 4, 5, 6, 7, 8. Last picture: HUVEC fed with PromoCell Endothelial Cell Growth Medium as positive control (9).

FIG. 4: Quantification of tube formation of 8 batches. Tube formation as described and illustrated in FIG. 3 was quantified for the analyzed samples using the software program ImageJ.

Figure 5:
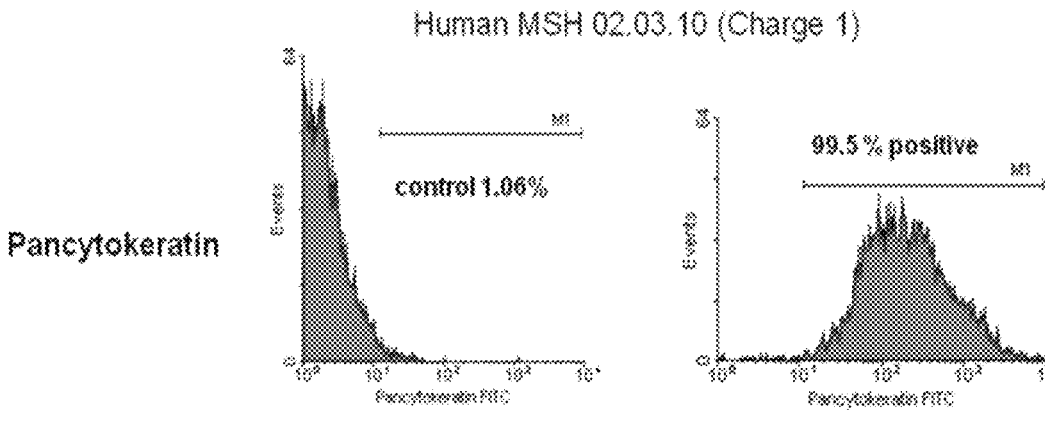

FIG. 5: Example of phenotype analysis via flow cytometry for oral mucosa cells. The example shows results for the first analysed sample (human MSH 02.03.10 (Charge 1)).

Figure 7:
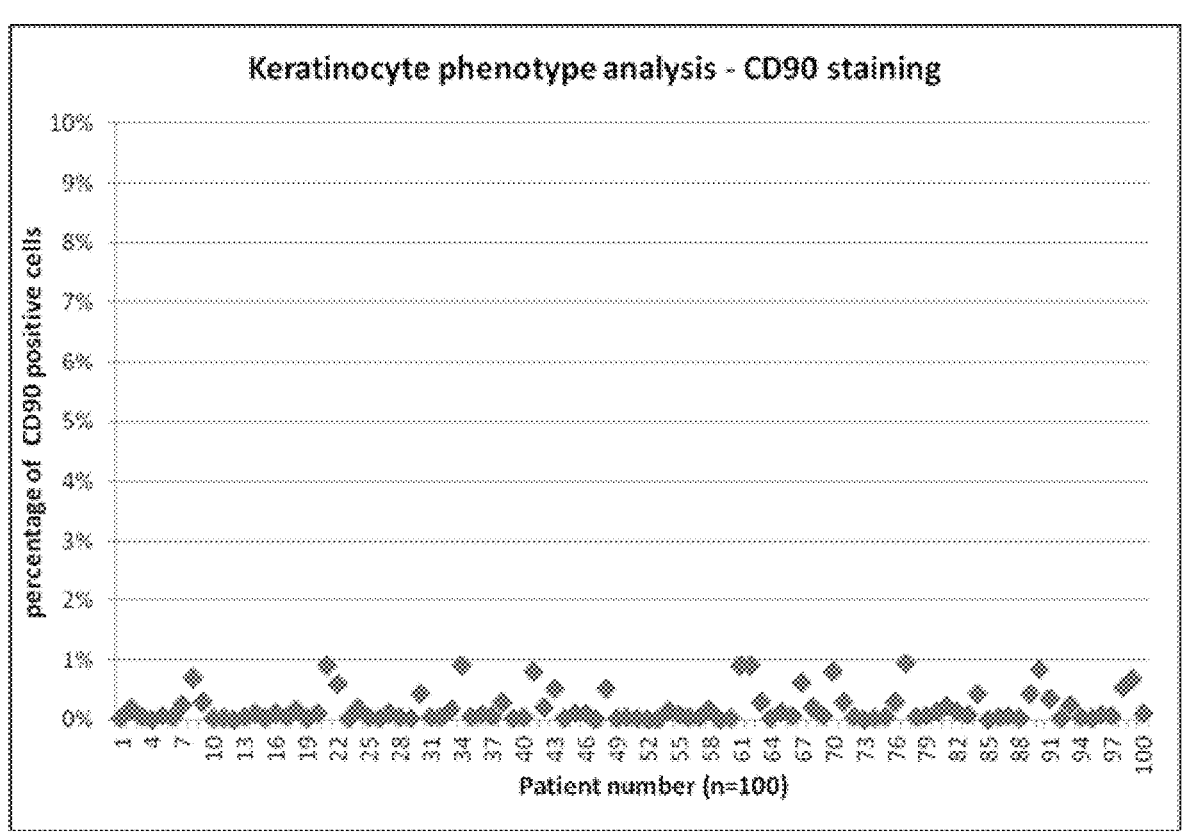

FIG. 6: Compilation of all determined percentages of pan-cytokeratin expression (Confirmation of cell identity). FIG. 7 presents the results of 100 independent batches of oral mucosal cells regarding the expression of pan-cytokeratin. One hundred independent patient charges were analyzed and for each batch The mean percentage of pan-cytokeratin expression in all 100 analyzed cultures was 98.2%.

FIG. 7: Compilation of all determined percentage CD90 values (Confirmation of cell purity.)

The invention claimed is:

1. A method for selecting oral mucosa tissue for production of transplantable oral mucosa tissue, wherein cells are cultured on a surface of a support, wherein at least one
   potency marker is selected from at least one vascular endothelial growth factor (VEGF) having a threshold value of more than or equal to 10 µg/ml in supernatant after 24 h of seeding on the surface
and at least one
   purity marker is selected from at least one acidic and basic (Type I and II) subfamilies of cytokeratins, wherein the amount of epithelial cells is more than or equal to 70%, optionally 80%,
and/or at least one
   impurity marker is selected from at least one Cluster Differentiation 90, wherein the amount of non-epithelial cells is less than or equal to 30%, optionally 20%, wherein the markers are determined in vitro.

2. The method for selecting oral mucosa tissue according to claim 1, wherein the purity marker is selected from at least one acidic and basic (Type I and II) subfamilies of cytokeratins, wherein the amount of epithelial cells is more than or equal to 95%, and/or the impurity marker is selected from at least one Cluster Differentiation 90, wherein the amount of non-epithelial cells is less than or equal to 5%.

3. The method for selecting oral mucosa tissue according to claim 1, wherein first, the oral mucosa cells derived from a tissue biopsy are multiplied in a culture, and, second the cells are cultured on a surface of a support.

4. The method for selecting oral mucosa tissue according to claim 1, wherein the cells are cultured on the surface of a support having a density of at least $1.0 \times 10E5$ to $1.6 \times 10E5$ cells, optionally at least $1.3 \times 10E5$ cells/cm$^2$.

5. The method for selecting oral mucosa tissue according to claim 1, wherein the proportion of fibroblasts in the isolated oral mucosa tissue in relation to the total cell number is less than or equal to 20%, optionally less than or equal to 5%.

6. The method for selecting oral mucosa tissue according to claim 1, wherein at least one potency marker is selected from at least one vascular endothelial growth factor (VEGF) having a threshold value of more than or equal to 10 µg/ml in the supernatant after 48 h of seeding on the surface.

7. The method for selecting oral mucosa tissue according to claim 1, wherein the support comprises a dissolvable membrane consisting of one or more biodegradable polymers, optionally biocompatible polymers or water-soluble polymers.

8. The method for selecting oral mucosa tissue according to claim 7, wherein the support comprises biodegradable polymers selected from the group of biological or non-biological origin, alpha-hydroxy acids, lactic acid and/or glycolic acid, polylactides, polyglycolides, polylactide-co-glycolides, and copolymers with polyethylene glycol, polyanhydrides, poly(ortho)esters, polyurethanes, Polyglycolic acids, Polylactic acids, Polycaprolactone, polybutyric acids, polyvaleric acids, polylactide-co-caprolactones, polyvinyl pyrrolidone (PVP), glycans, glycosaminoglycans and polysaccharides, such as pullulan, hyaluronan, gellan, cellulose, chitosan, alginate, and collagen.

9. The method for selecting oral mucosa tissue according to claim 1, for producing an autologous oral mucosa graft or tissue.

10. A graft or transplant comprising oral mucosa obtainable by the method according to claim 9 or isolated oral mucosa tissue thereof.

11. The graft or transplant comprising oral mucosa tissue according to claim 10 for treatment of one or more oral mucosa defects and/or diseases selected from vascular disorders, including diabetic foot, ulcer due to atherosclerosis, as well as diseases which require additional tissue for reconstruction, optionally skin burns, shrunken bladder, bladder dystrophy, small bladder after excision of bladder tumors, esophageal atresia, missing tissue after excision of esophagus tumor, ureteral stricture, ureteral tumor, urethra diseases, optionally urethral stricture, urethra malformation, hypospadias, corneal diseases, optionally limbal stem cell deficiency, cornea injury, and optionally having a scaffold or matrix.

12. The graft or transplant comprising oral mucosa tissue according to claim 10, wherein the oral mucosa tissue is fixed on the support, wherein the support is a dissolvable, self-dissolvable membrane or a biodegradable membrane.

13. An applicator comprising the graft or transplant according to claim 10.

14. Isolated oral mucosa tissue obtainable by a method according to claim 1.

15. Isolated oral mucosa tissue obtainable by the method according to claim 14, wherein a proportion of fibroblasts in the isolated oral mucosa tissue in relation to the total cell number is less than or equal to 5%.

16. Isolated oral mucosa tissue obtainable by the method according to claim 14, wherein the proportion of lymphocytes and adipocytes in the isolated oral mucosa tissue in relation to the total cell number is less than or equal to 1%.

\* \* \* \* \*